(12) United States Patent
Murayama et al.

(10) Patent No.: US 11,701,200 B2
(45) Date of Patent: Jul. 18, 2023

(54) WIRELESS IC TAG-ATTACHED METAL MEDICAL INSTRUMENT

(71) Applicant: Murata Manufacturing Co., Ltd., Nagaokakyo (JP)

(72) Inventors: Hiromi Murayama, Nagaokakyo (JP); Kengo Matsumoto, Nagaokakyo (JP); Tsuyoshi Suesada, Nagaokakyo (JP); Makoto Yasutake, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 0 days.

(21) Appl. No.: 17/550,569

(22) Filed: Dec. 14, 2021

(65) Prior Publication Data

US 2022/0096202 A1   Mar. 31, 2022

Related U.S. Application Data

(63) Continuation of application No. PCT/JP2020/032275, filed on Aug. 27, 2020.

(30) Foreign Application Priority Data

Oct. 18, 2019  (JP) ................................. 2019-191273

(51) Int. Cl.
*A61B 90/98* (2016.01)
*G06K 7/10* (2006.01)
(Continued)

(52) U.S. Cl.
CPC .......... *A61B 90/98* (2016.02); *G06K 7/10366* (2013.01); *G06K 19/0723* (2013.01);
(Continued)

(58) Field of Classification Search
CPC . A61B 90/98; G06K 7/10366; G06K 19/0723
(Continued)

(56) References Cited

U.S. PATENT DOCUMENTS

| 11,596,291 B2 * | 3/2023 | Harris ...................... H01Q 1/22 |
| 2006/0145871 A1 | 7/2006 | Donati et al. |

(Continued)

FOREIGN PATENT DOCUMENTS

| CN | 112955990 A | 6/2021 |
| JP | 4069958 B2 | 4/2008 |

(Continued)

OTHER PUBLICATIONS

International Search Report issued for PCT/JP2020/032273, dated Nov. 2, 2020.

(Continued)

*Primary Examiner* — Allyson N Trail
(74) *Attorney, Agent, or Firm* — ArentFox Schiff LLP

(57) ABSTRACT

A medical instrument is provided in which a wireless IC tag is fixed to a first or second body, such that at least part of the wireless IC tag is positioned more frontward than a front end of a first ring and a front end of a second ring and more backward than a support. A winding axis of an inductor is orthogonal to the up-down direction and intersects the front-back direction so that electric, magnetic, or electromagnetic field coupling is established between a resonant circuit and a metal medical instrument. Moreover, the metal medical instrument either emits a transmission signal, which has a frequency equal to a predetermined resonant frequency and supplied from the resonant circuit, as an electromagnetic wave, or it receives a reception signal having a frequency equal to the predetermined resonant frequency as an electromagnetic wave, and supplies the reception signal to the resonant circuit.

20 Claims, 6 Drawing Sheets

(51) Int. Cl.
  *G06K 19/07* (2006.01)
  *G06K 19/077* (2006.01)
  *H01F 27/06* (2006.01)
  *H01Q 1/22* (2006.01)
(52) U.S. Cl.
  CPC ........ *G06K 19/07758* (2013.01); *H01F 27/06* (2013.01); *H01Q 1/2225* (2013.01)
(58) Field of Classification Search
  USPC ........................................................ 235/492
  See application file for complete search history.

(56) References Cited

U.S. PATENT DOCUMENTS

| | | | | |
|---|---|---|---|---|
| 2008/0238631 | A1* | 10/2008 | Blake | A61B 90/92 340/10.51 |
| 2010/0289626 | A1* | 11/2010 | Oberle | G06K 7/0008 340/10.42 |
| 2017/0258551 | A1 | 9/2017 | Smith et al. | |
| 2020/0031067 | A1 | 1/2020 | Itakura et al. | |
| 2020/0160005 | A1 | 5/2020 | Volpi et al. | |
| 2021/0077111 | A1* | 3/2021 | Adams | A61B 17/3211 |
| 2022/0096202 | A1* | 3/2022 | Murayama | H01Q 7/00 |
| 2022/0104918 | A1* | 4/2022 | Matsumoto | H01Q 1/44 |
| 2022/0108144 | A1* | 4/2022 | Matsumoto | G06K 19/07771 |
| 2022/0287797 | A1* | 9/2022 | Hoegerle | G06K 19/0723 |
| 2022/0328170 | A1* | 10/2022 | Bilsøe | A61B 34/30 |
| 2022/0395340 | A1* | 12/2022 | Dumpe | A61B 90/96 |
| 2022/0395344 | A1* | 12/2022 | Wham | A61B 34/70 |

FOREIGN PATENT DOCUMENTS

| | | |
|---|---|---|
| JP | 2019185494 A | 10/2019 |
| WO | 2018181526 A1 | 10/2018 |
| WO | 2019004439 A1 | 1/2019 |

OTHER PUBLICATIONS

International Search Report issued for PCT/JP2020/032275, dated Nov. 2, 2020.
International Search Report issued for PCT/JP2020/032274, dated Nov. 2, 2020.
Written Opinion of the International Searching Authority issued for PCT/JP2020/032274, dated Nov. 2, 2020.

* cited by examiner

WIRELESS IC TAG-ATTACHED METAL MEDICAL INSTRUMENT

CROSS REFERENCE TO RELATED APPLICATIONS

The present application is a continuation of PCT/JP2020/032275 filed Aug. 27, 2020, which claims priority to Japanese Patent Application No. 2019-191273, filed Oct. 18, 2019, the entire contents of each of which are incorporated herein by reference.

TECHNICAL FIELD

The present invention relates to a wireless IC tag-attached metal medical instrument including a wireless IC tag and a metal medical instrument.

BACKGROUND

Conventional wireless IC tags are known, for example, as described in Japanese Patent No. 4069958 (hereinafter "Patent Literature 1"). The wireless IC device disclosed therein includes a wireless IC chip, a resonant circuit, and an antenna. The resonant circuit is connected to the wireless IC chip. The resonant circuit has a predetermined resonant frequency. Moreover, the antenna transmits a transmission signal supplied from the resonant circuit and/or receives a reception signal and supplies the reception signal to the resonant circuit.

Meanwhile, it has been proposed to use the wireless IC device described in Patent Literature 1 in the field of metal medical instruments. Specifically, it has been proposed that a wireless IC tag is attached to a metal medical instrument, such as scissors or forceps, to be used as a wireless IC device. In this case, the metal medical instrument functions as an antenna. As a result, management of the metal medical instrument becomes easy. Such a wireless IC device is required to suppress variations in communication distance of the wireless IC device.

SUMMARY OF THE INVENTION

Therefore, it is an object of the present invention to provide a wireless IC tag-attached metal medical instrument constructed to suppress variations in communication distance of the wireless IC tag-attached metal medical instrument.

According to an exemplary embodiment, a metal medical instrument, such as scissors and forceps, has, for example, a structure to be described below. Specifically, the metal medical instrument includes a first body portion, a second body portion, a support portion, a first ring portion, and a second ring portion. The first body portion and the second body portion extend in a front-back direction. The first body portion has a first end (i.e., a back end) and a second end (i.e., a front end). The second body portion has a third end (i.e., a back end) and a fourth end (i.e., a front end). The support portion supports the first body portion and the second body portion, such that the first body portion rotates relative to the second body portion. The first ring portion is connected to the first end of the first body portion. The second ring portion is connected to the third end of the second body portion.

In the above exemplary metal medical instrument, flat portions having a relatively large area are present in the vicinity of the first end, which is a connection portion between the first body portion and the first ring portion, and in the vicinity of the third end which is a connection portion between the second body portion and the second ring portion. Thus, in general, when a wireless IC tag is fixed to the metal medical instrument, the wireless IC tag is fixed to the vicinity of the first end or the vicinity of the third end. As a result, the wireless IC tag is constructed to be easily fixed to the metal medical instrument.

However, the inventor of the present application has found that variations in communication distance of a wireless IC tag-attached metal medical instrument occurs if the wireless IC tag is fixed to the vicinity of the first end or the vicinity of the third end for reasons to be described below. More specifically, the flat portions having a relatively large area are present in the vicinity of the first end, which is the connection portion between the first body portion and the first ring portion, and in the vicinity of the third end which is the connection portion between the second body portion and the second ring portion. If the wireless IC tag is fixed to the flat portion having a relatively large area, variations are likely to occur in a direction of the wireless IC tag. Thus, variations occur in coupling between the wireless IC tag and the metal medical instrument. As a result, variations are likely to occur in the communication distance of the wireless IC tag-attached metal medical instrument.

Therefore, an exemplary embodiment of the present invention fixes the wireless IC tag so as to satisfy the following conditions.

At least a part of the wireless IC tag is positioned more frontward than a front end of the first ring portion and a front end of the second ring portion and more backward than the support portion.

Moreover, a winding axis of an inductor of the wireless IC tag is orthogonal to an up-down direction and intersects the front-back direction.

The first body portion and the second body portion extend in the front-back direction in a region (hereinafter, referred to as a "first region") located more frontward than the front end of the first ring portion and the front end of the second ring portion and more backward than the support portion. The first region of each of the first body portion and the second body portion often has a thin rod shape. Therefore, a difficulty level of fixing the wireless IC tag to the first region of the first body portion or the second body portion is higher than a difficulty level of fixing the wireless IC tag to the vicinity of the first end or the vicinity of the third end. Thus, those skilled in the art hesitate to fix the wireless IC tag to the first region of the first body portion or the second body portion.

However, the exemplary embodiment of the present invention preferably fixes the wireless IC tag to the first region of the first body portion or the second body portion as will be described below. More specifically, the first region of the first body portion and the second body portion has the thin rod shape, and thus, often has a thin flat portion. A difficulty level of fixing the wireless IC tag to the thin flat portion is slightly higher than a difficulty level of fixing the wireless IC tag to a wide flat portion. However, a direction of the wireless IC tag to which the wireless IC tag can be fixed is limited in the thin flat portion. Thus, the inventor of the present application has noticed that a difficulty level of fixing the wireless IC tag to the thin flat portion in an accurate direction is lower than a difficulty level of fixing the wireless IC tag to the wide flat portion in an accurate direction. That is, the inventor of the present application has found that the first region is more preferable than the vicinity of the first end and the vicinity of the third end when the wireless IC tag is fixed to the first body portion or the second body portion in an accurate direction.

Further, according to the exemplary embodiment of the present invention, the inductor of the wireless IC tag and the first body portion or the second body portion can be effectively coupled by fixing the wireless IC tag to the first body or the second body such that the winding axis of the inductor of the wireless IC tag is orthogonal to the up-down direction and intersects the front-back direction. More specifically, when the winding axis of the inductor of the wireless IC tag is orthogonal to the up-down direction and intersects the front-back direction, the winding axis of the inductor of the wireless IC intersects the first region of the first body portion and the second body portion. As a result, a magnetic flux generated by the inductor of the wireless IC tag makes a circle around the first region of the first body portion and the second body portion. As a result, a current is easily generated in the first region of the first body portion and the second body portion by electromagnetic induction. Moreover, the metal medical instrument easily functions as an antenna. As described above, the occurrence of the variations in the communication distance of the wireless IC tag-attached metal medical instrument is suppressed.

In order to solve the above-described problem, the exemplary embodiment of the present invention has the following configuration.

Specifically, a wireless IC tag-attached metal medical instrument (1) is provided that includes a wireless IC tag including a resonant circuit, which includes an inductor having a winding axis, and a wireless IC chip. Moreover, the resonant circuit is electrically connected to the wireless IC chip and has a predetermined resonant frequency.

In an exemplary aspect, the metal medical instrument includes a first body portion (also referred to as a "first body") that is made of metal and has a first end and a second end; a second body portion (also referred to as a "second body") that is made of metal and has a third end and a fourth end; and a support portion that has a central axis extending in an up-down direction. Moreover, the support portion supports the first body portion and the second body portion, such that a distance between the first end and the third end and a distance between the second end and the fourth end change as the first body portion rotates about the central axis relative to the second body portion. The support portion supports the first body portion and the second body portion such that the first body portion and the second body portion extend in a front-back direction when the first end and the third end are closest to each other. A first ring portion (also referred to as a "first ring") is connected to the first end of the first body portion and into which a finger of an operator is inserted; and a second ring portion (also referred to as a "second ring") is connected to the third end of the second body portion and into which a finger of the operator is inserted.

Electric field coupling, magnetic field coupling, or electromagnetic field coupling is established between the resonant circuit and the metal medical instrument. Moreover, the metal medical instrument is configured to perform either (A) and/or (B) as the wireless IC tag is fixed to the first body or the second body, such that at least a part of the wireless IC tag is positioned more frontward than a front end of the first ring portion and a front end of the second ring portion and more backward than the support portion when the first end and the third end are closest to each other and the winding axis of the inductor is orthogonal to the up-down direction and intersects the front-back direction when the first end and the third end are closest to each other.

The metal medical instrument is configured to emit a transmission signal, which has a frequency equal to the predetermined resonant frequency and is supplied from the resonant circuit, as an electromagnetic wave.

The metal medical instrument receives a reception signal having a frequency equal to the predetermined resonant frequency as an electromagnetic wave, and supplies the reception signal to the resonant circuit.

According to the wireless IC tag-attached metal medical instrument (1), variations in communication distance of the wireless IC tag-attached metal medical instrument can be suppressed. More specifically, in the wireless IC tag-attached metal medical instrument (1), the wireless IC tag is fixed to the first body portion or the second body portion, such that at least apart of the wireless IC tag is positioned more frontward than the front end of the first ring portion and the front end of the second ring portion and more backward than the support portion when the first end and the third end are closest to each other, and the winding axis of the inductor is orthogonal to the up-down direction and intersects the front-back direction when the first end and the third end are closest to each other. Thus, the electric field coupling, magnetic field coupling, or electromagnetic field coupling is established between the resonant circuit and the metal medical instrument. Hereinafter, a region located more frontward than the front end of the first ring portion and the front end of the second ring portion and more backward than the support portion is referred to as a first region. The first region of the first body portion and the second body portion has a thin rod shape, and thus, often has a thin flat portion. A difficulty level of fixing the wireless IC tag to the thin flat portion is slightly higher than a difficulty level of fixing the wireless IC tag to a wide flat portion. However, a direction of the wireless IC tag to which the wireless IC tag can be fixed is limited in the thin flat portion. Thus, a difficulty level of fixing the wireless IC tag to the thin flat portion in an accurate direction is lower than a difficulty level of fixing the wireless IC tag to the wide flat portion in an accurate direction. As a result, the wireless IC tag is fixed to the metal medical instrument in the accurate direction and variations in the communication distance of the wireless IC tag-attached metal medical instrument are suppressed.

Further, in the wireless IC tag-attached metal medical instrument (1), the wireless IC tag is fixed to the first body portion or the second body portion such that the winding axis of the inductor of the wireless IC tag is orthogonal to the up-down direction and intersects the front-back direction. As a result, the inductor of the wireless IC tag can be effectively coupled with the first body portion or the second body portion. More specifically, when the winding axis of the inductor of the wireless IC tag is orthogonal to the up-down direction and intersects the front-back direction, the winding axis of the inductor of the wireless IC intersects the first region of the first body portion and the second body portion. As a result, a magnetic flux generated by the inductor of the wireless IC tag makes a circle around the first region of the first body portion and the second body portion. A current is easily generated in the first region of the first body portion and the second body portion by electromagnetic induction. As a result, the metal medical instrument is configured to easily function as an antenna. As described above, the occurrence of the variations in the communication distance of the wireless IC tag-attached metal medical instrument is suppressed.

Moreover, a wireless IC tag-attached metal medical instrument (2) is the wireless IC tag-attached metal medical instrument (1) in which the winding axis of the inductor is orthogonal to the up-down direction and the front-back direction when the first end and the third end are closest to each other.

In the wireless IC tag-attached metal medical instrument (2), the winding axis of the inductor is orthogonal to the up-down direction and the front-back direction when the first end and the third end are closest to each other. Thus, a current is more easily generated in the first region of the first body portion and the second body portion by electromagnetic induction. As a result, the metal medical instrument is configured to easily function as an antenna. Accordingly, the occurrence of the variations in the communication distance of the wireless IC tag-attached metal medical instrument is suppressed.

A wireless IC tag-attached metal medical instrument (3) is the wireless IC tag-attached metal medical instrument (1) or (2) in which the metal medical instrument is a general medical device belonging to Class I in the Japanese Medical Device Nomenclature.

It is recommended to attach the wireless IC tag to a general medical device belonging to Class I in the Japanese medical device name. Therefore, in the wireless IC tag-attached metal medical instrument (3), the metal medical instrument is the general medical device belonging to Class I in the Japanese Medical Device Nomenclature.

A wireless IC tag-attached metal medical instrument (4) is the wireless IC tag-attached metal medical instrument (1) to (3) in which the metal medical instrument is a small steel article.

It is recommended to attach the wireless IC tag to a small steel article. Therefore, in the wireless IC tag-attached metal medical instrument (4), the metal medical instrument is the small steel article.

A wireless IC tag-attached metal medical instrument (5) is the wireless IC tag-attached metal medical instrument (1) to (4) in which the wireless IC tag is fixed to the first body portion or the second body portion with a resin adhesive.

According to the wireless IC tag-attached metal medical instrument (5), the wireless IC tag is fixed to the first body portion or the second body portion of the metal medical instrument with the resin adhesive, and thus, a fixing member or the like for fixing the wireless IC tag to the first body portion or the second body portion is unnecessary. Thus, it is easy to fix the wireless IC tag to the first body portion or the second body portion.

A wireless IC tag-attached metal medical instrument (6) is the wireless IC tag-attached metal medical instrument (1) to (4) in which the wireless IC tag is fixed to the first body portion or the second body portion by welding.

According to the wireless IC tag-attached metal medical instrument (6), the wireless IC tag is fixed to the first body portion or the second body portion of the metal medical instrument by welding, and thus, detachment of the wireless IC tag from the first body portion or the second body portion due to an environmental change, such as a temperature change, is reduced.

A wireless IC tag-attached metal medical instrument (7) is the wireless IC tag-attached metal medical instrument (6).

In an exemplary aspect, the wireless IC tag has a rectangular shape when viewed in a downward direction.

In an exemplary aspect, a long side of the wireless IC tag extends in the front-back direction when viewed in the downward direction.

In an exemplary aspect, the wireless IC tag is fixed to the first body portion or the second body portion via a fixing member welded to the first body portion or the second body portion.

In an exemplary aspect, a welded portion where the fixing member is welded to the first body portion or the second body portion is positioned in front of or at the back of the wireless IC tag.

A wireless IC tag-attached metal medical instrument (8) is the wireless IC tag-attached metal medical instrument (1) to (7).

In an exemplary aspect, the wireless IC tag-attached metal medical instrument further includes a resin portion, and the resin portion covers the wireless IC tag so that the wireless IC tag is not exposed.

In the wireless IC tag-attached metal medical instrument (8), the wireless IC tag is covered with the resin portion. Thus, the wireless IC tag is protected by the resin portion.

A wireless IC tag-attached metal medical instrument (9) is the wireless IC tag-attached metal medical instrument (1) to (8) in which the predetermined resonant frequency belongs to an ultrahigh frequency (UHF) frequency band.

A wireless IC tag-attached metal medical instrument (10) is the wireless IC tag-attached metal medical instrument (1) to (9). The wireless IC tag-attached metal medical instrument is configured to communicate with a reader/writer via an electromagnetic wave.

The above-described object and other objects, features, aspects, and advantages of the exemplary embodiment present invention will become more apparent from the following detailed description of an embodiment of the present invention given with reference to the accompanying drawings.

It is noted that as used in the present specification, the term "and/or" includes any and all combinations of one or a plurality of the associated listed items.

Moreover, as used the present this specification, the terms "including", "comprising" or "having" and variations thereof specify the presence of stated features, steps, operations, elements, components, and/or their equivalents, but may also include one or a plurality of steps, operations, elements, components, and/or groups thereof.

Unless otherwise defined, all terms (including technical and scientific terms) used in the present specification have the same meaning as commonly understood by those skilled in the art to which the present teaching belongs.

In the description of the exemplary embodiment, it will be understood that the number of techniques and the number of steps are disclosed. Each of these has individual benefit, and each can also be used in conjunction with one or more, or in some cases all, of the other disclosed techniques. Therefore, this description refrains from repeating every possible combination of the individual steps in an unnecessary fashion for the sake of clarity.

In the following description, for purposes of explanation, numerous specific details are set forth in order to provide a thorough understanding of the exemplary embodiment of the present invention. However, it will be apparent to those skilled in the art that the present invention can be practiced without these specific details. The present disclosure is to be considered as an illustration of the present invention, and is not intended to limit the present invention to the specific embodiments illustrated by the following drawings or description.

According to the present invention, the variations in the communication distance of the wireless IC tag-attached metal medical instrument can be suppressed.

DETAILED DESCRIPTION OF EMBODIMENTS

Exemplary Embodiment

[Configuration of Wireless IC Tag-Attached Metal Medical Instrument]

Figure 1:
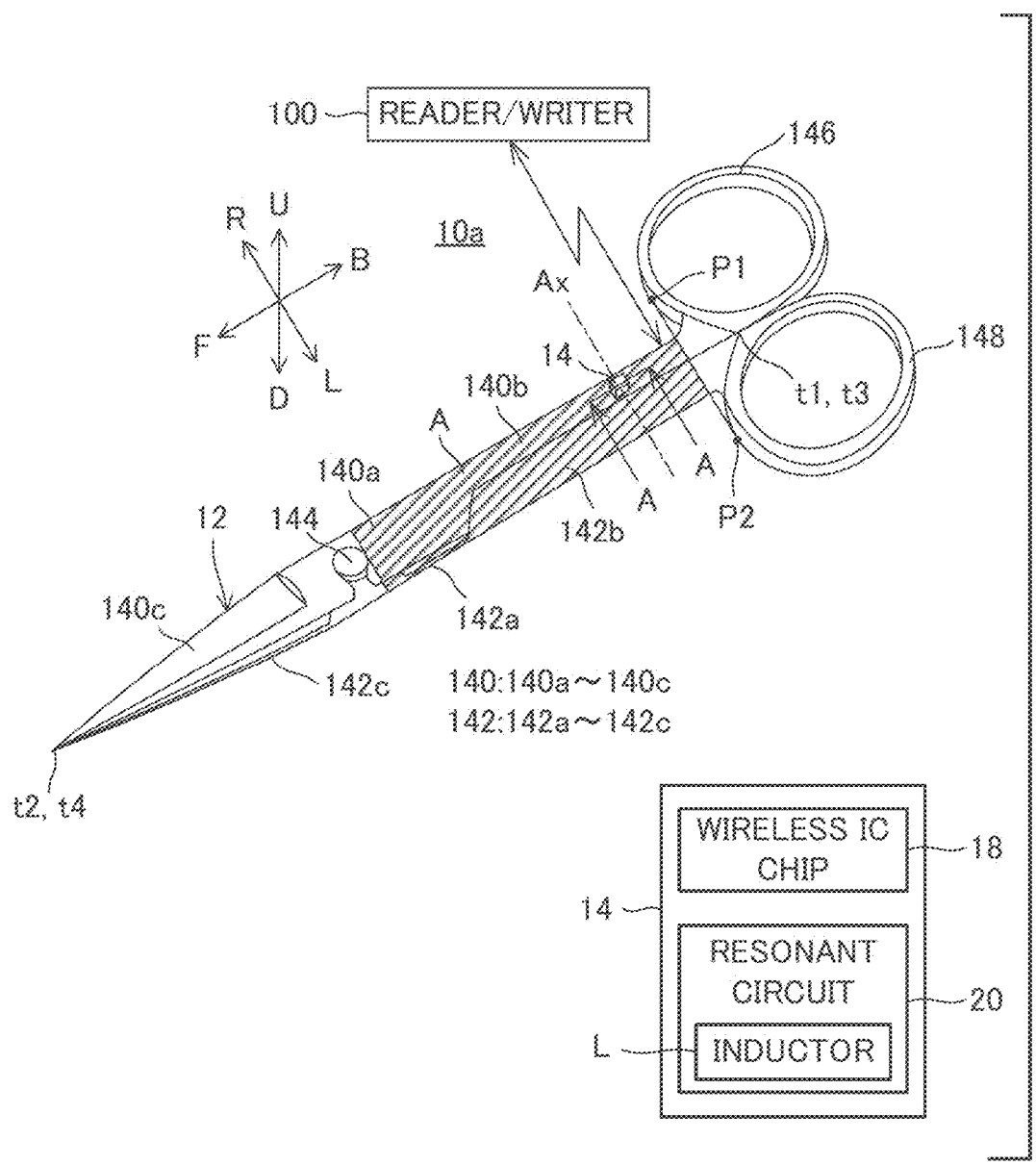
FIG. 1 is an external perspective view of a wireless IC tag-attached metal medical instrument 10a according to an exemplary embodiment.
Figure 2:
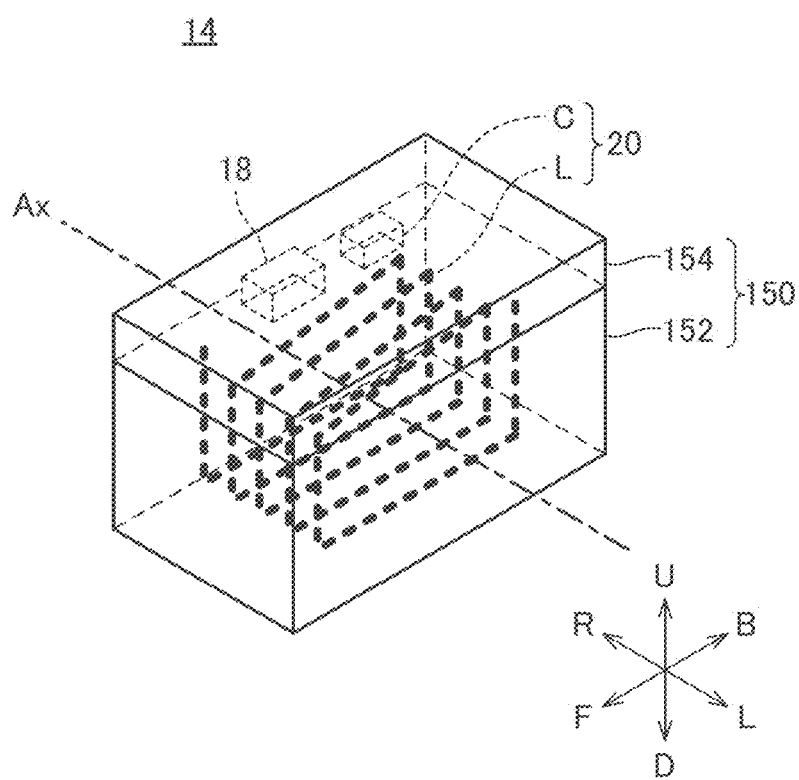
FIG. 2 is a perspective view of a wireless IC tag 14.
Figure 3:
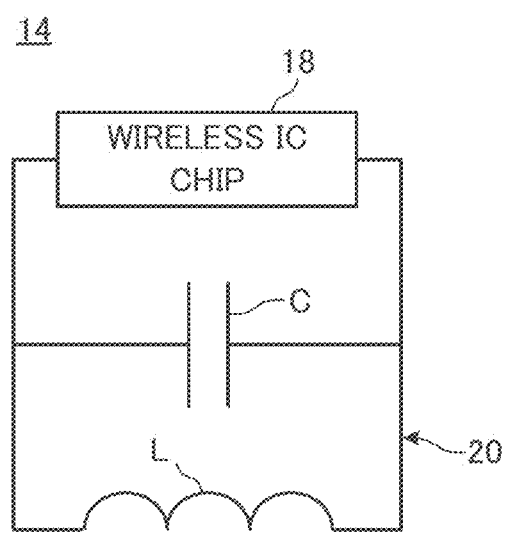
FIG. 3 is an equivalent circuit diagram of the wireless IC tag 14.
Figure 4:
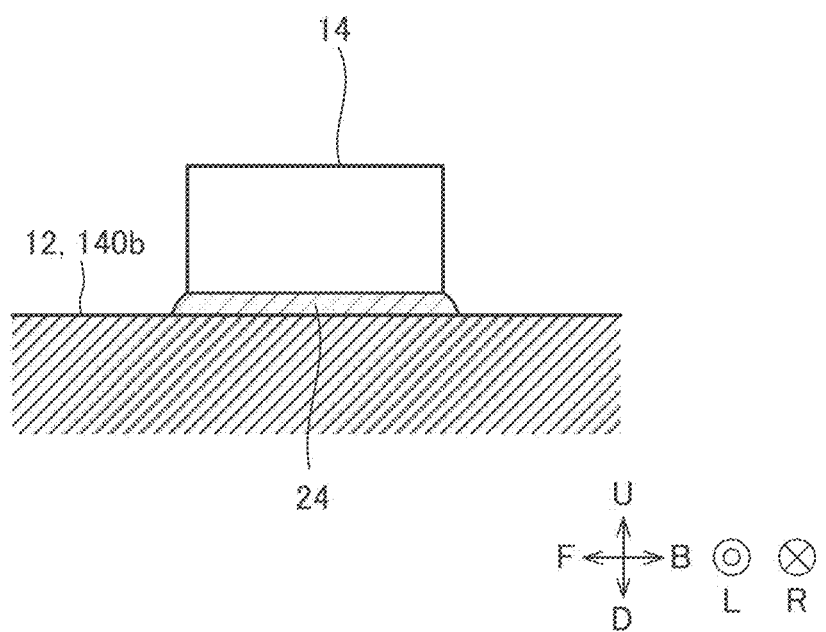
FIG. 4 is a cross-sectional view taken along line A-A in FIG. 1.

Next, a wireless IC tag-attached metal medical instrument 10a according to an exemplary embodiment will be described with reference to the drawings. FIG. 1 is an external perspective view of the wireless IC tag-attached metal medical instrument 10a according to the embodiment. Note that FIG. 1 also illustrates a block diagram of a wireless IC tag 14. FIG. 2 is a perspective view of the wireless IC tag 14. FIG. 3 is an equivalent circuit diagram of the wireless IC tag 14. FIG. 4 is a cross-sectional view taken along line A-A in FIG. 1.

In the present specification, an axis or a member extending in a front-back direction does not necessarily indicate only the axis or member parallel to the front-back direction. The axis or member extending in the front-back direction is the axis or member inclined within a range of ±45° with respect to the front-back direction. Similarly, an axis or a member extending in an up-down direction is the axis or member inclined within a range of ±45° with respect to the up-down direction. An axis or a member extending in a left-right direction is the axis or member inclined within a range of ±45° with respect to the left-right direction.

In the present specification, a case where a first member is supported by a second member includes a case where the first member is attached to the second member so as to be immovable with respect to the second member (i.e., fixed) and a case where the first member is attached to the second member so as to be movable with respect to the second member. The case where the first member is supported by the second member further includes both of a case where the first member is directly attached to the second member and a case where the first member is attached to the second member with a third member interposed therebetween. It is also noted that the first member, the second member, and the third member are included in the wireless IC tag-attached metal medical instrument 10a.

In the present specification, the first member and the second member arrayed in the front-back direction indicate the following state. Both the first member and the second member are in the state of being disposed on an arbitrary straight line indicating the front-back direction when the first member and the second member are viewed in a direction perpendicular to the front-back direction. In the present specification, the first member and the second member arrayed in the front-back direction when viewed in the up-down direction indicate the following state. Both the first member and the second member are disposed on an arbitrary straight line indicating the front-back direction when the first member and the second member are viewed in the up-down direction. In this case, anyone of the first member and the second member is not necessarily disposed on an arbitrary straight line indicating the front-back direction when the first member and the second member are viewed from the left-right direction different from the up-down direction. Note that the first member and the second member may be in contact with each other. The first member and the second member may be separated from each other. The third member may be present between the first member and the second member. It should be appreciated that this definition also applies to directions other than the front-back direction.

In the present specification, the first member disposed in front of the second member indicates the following state. At least a part of the first member is disposed in a region through which the second member passes at the time of moving in parallel in the forward direction. Accordingly, the first member may be accommodated in the region through which the second member passes at the time of moving in parallel in the forward direction, or may protrude from the region through which the second member passes at the time of moving in parallel in the forward direction. In this case, the first member and the second member are arrayed in the front-back direction. This definition also applies to directions other than the front-back direction.

In the present specification, the first member being disposed in front of the second member when viewed in the left-right direction indicates the following state. The first member and the second member are arrayed in the front-back direction when viewed in the left-right direction, and a portion of the first member facing the second member is disposed in front of the second member when viewed in the left-right direction. In this definition, the first member and the second member are not necessarily arrayed in the front-back direction in three dimensions. This definition also applies to directions other than the front-back direction.

In the present specification, the first member disposed more frontward than the second member indicates the following state. The first member is disposed in front of a plane which passes through a front end of the second member and is orthogonal to the front-back direction. In this case, the first member and the second member may be arrayed or are not necessarily arrayed in the front-back direction. It should be appreciated that this definition also applies to directions other than the front-back direction.

In the present specification, each portion of the first member is defined as follows unless otherwise specified. A front portion of the first member means the front half of the first member. A back portion of the first member means the back half of the first member. A left portion of the first member means the left half of the first member. A right portion of the first member means the right half of the first member. An upper portion of the first member means the upper half of the first member. A lower portion of the first member means the lower half of the first member. A front end of the first member means an end of the first member in the forward direction. A back end of the first member means an end of the first member in the backward direction. A left end of the first member means an end of the first member in the leftward direction. A right end of the first member means an end of the first member in the rightward direction. An upper end of the first member means an end of the first member in the upward direction. The lower end of the first member means an end of the first member in the downward direction. A front end portion of the first member means the front end of the first member and the vicinity thereof. A back end portion of the first member means the back end of the first member and the vicinity thereof. A left end portion of the first member means the left end of the first member and the vicinity thereof. A right end portion of the first member means the right end of the first member and the vicinity thereof. An upper end portion of the first member means the upper end of the first member and the vicinity thereof. A lower end portion of the first member means the lower end of the first member and the vicinity thereof.

Hereinafter, a front-back direction of the wireless IC tag-attached metal medical instrument 10a is referred to as the front-back direction. The front-back direction is a direction in which blades of scissors as the wireless IC tag-attached metal medical instrument 10a extend. An up-down direction of the wireless IC tag-attached metal medical instrument 10a is referred to as the up-down direction. The up-down direction is a direction in which the two blades of the scissors as the wireless IC tag-attached metal medical instrument 10a overlap each other. A left-right direction of the wireless IC tag-attached metal medical instrument 10a is referred to as the left-right direction. A forward direction of the wireless IC tag-attached metal medical instrument 10a is referred to as the forward direction. A backward direction of the wireless IC tag-attached metal medical instrument 10a is referred to as the backward direction. A left direction of the wireless IC tag-attached metal medical instrument 10a is referred to as the left direction. A right direction of the wireless IC tag-attached metal medical instrument 10a is referred to as the right direction. An upward direction of the wireless IC tag-attached metal medical instrument 10a is referred to as the upward direction. A downward direction in the wireless IC tag-attached metal medical instrument 10a is referred to as the downward direction. Note that the up-down direction, the left-right direction, and the front-back direction are defined directions for convenience of the description and to facilitate an understanding of the invention. Therefore, the up-down direction, the left-right direction, and the front-back direction do not necessarily coincide with the actual up-down direction, left-right direction, and front-back direction at the time of using the wireless IC tag-attached metal medical instrument 10, respectively.

As illustrated in FIG. 1, the wireless IC tag-attached metal medical instrument 10a includes a metal medical instrument and the wireless IC tag 14. Note that the wireless IC tag-attached metal medical instrument 10a may further include a configuration other than the metal medical instrument 12 and the wireless IC tag 14.

It is recommended to attach the wireless IC tag 14 to a general medical device belonging to Class I in the Japanese medical device nomenclature. Therefore, the metal medical instrument 12 is, for example, a general medical device belonging to Class I in the Japanese medical device nomenclature. In addition, it is recommended to attach the wireless IC tag 14 to a small steel article. Therefore, the metal medical instrument 12 is, for example, a small steel article. The metal medical instrument 12 is, for example, a gag, a retractor, forceps, a needle holder, or scissors. In the present embodiment as shown, the metal medical instrument 12 is a pair of scissors. Therefore, the metal medical instrument 12 can be set to a state where two blades are separated (hereinafter, in an open state). In addition, the metal medical instrument 12 can be set to a state where the two blades overlap (hereinafter, in a closed state) as illustrated in FIG. 1.

The metal medical instrument 12 is made of metal. In the present embodiment, the entire metal medical instrument 12 is made of metal. Thus, the metal medical instrument 12 does not include a resin portion or a rubber portion. The metal medical instrument 12 may be made of, for example, steel, iron, copper, or another metal or an alloy. However, the metal medical instrument 12 may include a resin portion or a rubber portion.

As shown, the metal medical instrument 12 includes a first body portion 140, a second body portion 142, a support portion 144, a first ring portion 146, and a second ring portion 148. The first body portion 140 is a metal member having a first end t1 and a second end t2. The first body portion 140 extends in the front-back direction in the closed state of the metal medical instrument 12. The first end t1 is a back end of the first body portion 140. The second end t2 is a front end of the first body portion 140. The first body portion 140 includes a first supported portion 140a, a first straight portion 140b, and a first blade portion 140c. The second body portion 142 is a metal member having a third end t3 and a fourth end t4. The second body portion 142 extends in the front-back direction in the closed state of the metal medical instrument 12. The third end t3 is a backend of the second body portion 142. The fourth end t4 is a front end of the second body portion 142. The second body portion 142 includes a second supported portion 142a, a second straight portion 142b, and a second blade portion 142c. Hereinafter, a structure of the metal medical instrument 12 in the closed state will be described.

The first supported portion 140a has a flat plate shape extending in the front-back direction. The second supported portion 142a has a flat plate shape extending in the front-back direction. The first supported portion 140a is disposed on the second supported portion 142a.

The first blade portion 140c has a flat plate shape extending in the forward direction from a front end of the first supported portion 140a. A blade is provided on a right side of the first blade portion 140c. The second blade portion 142c has a flat plate shape extending in the forward direction from a front end of the second supported portion 142a. A blade is provided on a left side of the second blade portion 142c. The first blade portion 140c is disposed on the second blade portion 142c.

As further shown, the first straight portion 140b has a bar shape extending in the backward direction from a back end of the first supported portion 140a. An upper surface and a lower surface of the first straight portion 140b are thin flat surfaces. The second straight portion 142b has a bar shape extending in the backward direction from a back end of the second supported portion 142a. An upper surface and a lower surface of the second straight portion 142b are thin flat surfaces. The first straight portion 140b is disposed to the right of the second straight portion 142b. In this manner, the first straight portion 140b and the second straight portion 142b are disposed in the left-right direction.

The first ring portion 146 is connected to the first end t1 of the first body portion 140. That is, the first ring portion 146 is connected to a back end of the first straight portion 140b. The first ring portion 146 has an annular shape when viewed in the downward direction. As known to those skilled in the art, a finger of an operator can be inserted into the first ring portion 146. Although the first ring portion 146 is shown as having a circular or ring shape, additional types and structures of gripping members (e.g., plyer grips) can be used in alternative aspects.

The second ring portion 148 is connected to the third end t3 of the second body portion 142. That is, the second ring portion 148 is connected to a back end of the second straight portion 142b. The second ring portion 148 has an annular shape when viewed in the downward direction. A As known to those skilled in the art, a finger of the operator can be inserted into the second ring portion 148. The first ring portion 146 is disposed on the right of the second ring portion 148. Although the second ring portion 148 is shown as having a circular or ring shape, additional types and structures of gripping members (e.g., plyer grips) can be used in alternative aspects.

The support portion 144 has a central axis extending in the up-down direction. The support portion 144 supports the first body portion 140 and the second body portion 142 such that a distance between the first end t1 and the third end t3 and a distance between the second end t2 and the fourth end t4 change as the first body portion 140 rotates about the central axis of the support portion 144 relative to the second body portion 142. In addition, the support portion 144 supports the first body portion 140 and the second body portion 142 such that the first body portion 140 and the second body portion 142 extend in the front-back direction when the first end t1 and the third end t3 are closest to each other. The time when the first end t1 and the third end t3 are closest to each other is when the metal medical instrument 12 is in the closed state as illustrated in FIG. 1. The support portion 144 is, for example, a screw or bolt. The support portion 144 penetrates through the first supported portion 140a and the second supported portion 142a in the up-down direction. As a result, the second body portion 142 can rotate about the central axis of the support portion 144 relative to the first body portion 140. As a further result, the metal medical instrument 12 can be in the open state and the closed state. It is noted that the support portion 144 may be integrated with the first body portion 140 or the second body portion 142.

As illustrated in FIG. 1, the wireless IC tag 14 includes a wireless IC chip 18 and a resonant circuit 20. Note that the wireless IC tag 14 may further include a configuration other than the wireless IC chip 18 and the resonant circuit 20.

The resonant circuit 20 is electrically connected to the wireless IC chip 18. The resonant circuit 20 has a predetermined resonant frequency f0. The resonant circuit 20 is a resonant circuit including an inductor L having a winding axis Ax. An LC resonant circuit is an LC parallel resonant circuit in which a capacitor C and the inductor L are connected in parallel, or an LC series resonant circuit in which the capacitor C and the inductor L are connected in series. In the present embodiment, the resonant circuit 20 is the LC resonant circuit including the inductor L and the capacitor C as illustrated in FIGS. 2 and 3. The resonant frequency f0 is determined by a capacitance value of the capacitor C and an inductance value of the inductor L. When a high-frequency signal having a frequency equal to the resonant frequency f0 is input to the LC parallel resonant circuit, the impedance of the LC parallel resonant circuit is maximized. When the high-frequency signal having the frequency equal to the resonant frequency f0 is input to the LC series resonant circuit, the impedance of the LC series resonant circuit is minimized. In the present embodiment, the resonant circuit 20 is the LC parallel resonant circuit as illustrated in FIG. 3. It is noted that a parasitic capacitance may be used for the capacitor C. In this case, a chip capacitor as illustrated in FIG. 2 is unnecessary.

The resonant frequency f0 belongs to, for example, an ultrahigh frequency (UHF) frequency band. The UHF frequency band is a band to which a frequency of 300 MHz or more and 3 GHz or less belongs.

Next, a specific configuration of the wireless IC tag 14 will be described. The wireless IC tag 14 has a rectangular parallelepiped shape as illustrated in FIG. 2. Therefore, the wireless IC tag 14 has a rectangular shape when viewed in the downward direction. Then, a long side of the wireless IC tag 14 extends in the front-back direction when viewed in the downward direction. The wireless IC tag 14 includes the wireless IC chip 18, the resonant circuit 20, and a body 150.

The body 150 has a rectangular parallelepiped shape and includes a body lower portion 152 and a body upper portion 154. The body lower portion 152 is, for example, a laminate. The body lower portion 152 has a rectangular parallelepiped shape. The laminate has a structure in which a plurality of insulator layers having main surfaces perpendicular to the left-right direction are laminated in the left-right direction. However, a lamination direction of the laminate may be the up-down direction or the front-back direction. The laminate is made of, for example, a glass epoxy resin. The body upper portion 154 is, for example, a resin member. The body upper portion 154 has, for example, a rectangular parallelepiped shape. moreover, the resin member is made of, for example, an epoxy resin.

The wireless IC chip 18 is a semiconductor integrated circuit. The wireless IC chip 18 is mounted on an upper surface of the body lower portion 152. The wireless IC chip 18 includes a memory that stores predetermined information. In addition, the wireless IC chip 18 includes a modulator that modulates a carrier wave with transmission data stored in the memory to generate a transmission signal. In addition, the wireless IC chip 18 includes a demodulator that demodulates reception data from a reception signal obtained by modulating a carrier wave with the reception data.

The resonant circuit 20 includes a capacitor C and an inductor L. The capacitor C is a chip capacitor. The capacitor C is mounted on the upper surface of the body lower portion 152. The inductor L is provided in the body lower portion 152. The inductor L has a helix shape. As further shown, the helix shape is a three-dimensional shape. The inductor L has the winding axis Ax. The winding axis Ax extends in the left-right direction. The inductor L makes a circle about the winding axis Ax. The winding axis Ax is a line passing through a center of a region surrounded by the inductor L when viewed in the right direction. The center is, for example, the center of gravity. Note that the inductor L may have a spiral shape, which can be a two-dimensional shape.

The inductor L includes a plurality of conductor layers and a plurality of via-hole conductors. Specifically, each of the plurality of conductor layers is formed on main surfaces of the plurality of insulator layers. Each of the plurality of conductor layers makes a circle about the winding axis Ax when viewed in the right direction. Each of the plurality of via-hole conductors penetrates through the plurality of insulator layers in the left-right direction. Each of the plurality of via-hole conductors connects ends of conductor layers adjacent to each other in the left-right direction. Note that the inductor L makes a circle about a plurality of times. However, the inductor L may have, for example, a loop shape that makes a circle with a length less than one turn.

As illustrated in FIG. 3, the capacitor C and the inductor L are connected in parallel to the wireless IC chip 18 by a wiring (not illustrated in FIG. 2). Thus, the resonant circuit 20 is an LC parallel resonator.

Next, fixation of the wireless IC tag 14 to the metal medical instrument 12 will be described. The wireless IC tag 14 is fixed to the first body portion 140 or the second body portion 142 such that at least apart of the wireless IC tag 14 is positioned more frontward than the front end P1 of the first ring portion 146 and the front end P2 of the second ring portion 148 and more backward than the support portion 144 when the first end t1 and the third end t3 are closest to each other, and the winding axis Ax of the inductor L is orthogonal to the up-down direction and intersects the front-back direction when the first end t1 and the third end t3 are closest to each other. Thus, electric field coupling, magnetic field coupling, or electromagnetic field coupling is established between the resonant circuit 20 and the metal medical instrument 12, such that the metal medical instrument 12 is configured to perform functions (A) and/or (B) to be described later.

More specifically, a region, located more frontward than the front end P1 of the first ring portion 146 and the front end P2 of the second ring portion 148 and more backward than the support portion 144, in the closed state of the metal medical instrument 12 is defined as a first region A. At least a part of the wireless IC tag 14 is positioned in the first region A. In the present embodiment, the entire metal medical instrument 12 is positioned in the first region A. Further, when the metal medical instrument 12 is in the closed state, the winding axis Ax of the inductor L is orthogonal to the up-down direction and intersects the front-back direction. In the present embodiment, the winding axis Ax of the inductor L is orthogonal to the up-down direction and the front-back direction when the metal medical instrument 12 is in the closed state. That is, the winding axis Ax of the inductor L extends in the left-right direction as shown in FIG. 1. Note that a fact that two straight lines intersect each other means that the two straight lines are not parallel and the two straight lines are not in a twisted relationship. A fact that two straight lines are orthogonal to each other includes a case where the two straight lines form an angle slightly deviated from 90 degrees in addition to a case where the two straight lines form 90 degrees. For purposes of this disclosure, it is noted that the slightly deviated angle is, for example, 10 degrees.

As illustrated in FIG. 1, the wireless IC tag 14 is fixed to an upper surface of the first straight portion 140b. However, in alternative aspects, the wireless IC tag 14 may be fixed to the first region A of the first body portion 140 and the second body portion 142. Thus, the wireless IC tag 14 may be fixed to a lower surface of the first straight portion 140b. In addition, the wireless IC tag 14 may be fixed to an upper surface or a lower surface of the second straight portion 142b. In addition, the wireless IC tag 14 may be fixed to an upper surface of the first supported portion 140a or a lower surface of the second supported portion 142a. As illustrated in FIG. 4, the wireless IC tag 14 is fixed to the first body portion 140 with a resin adhesive 24. However, the wireless IC tag 14 may be fixed to the second body portion 142 with the resin adhesive 24.

In addition, the fact that the electric field coupling is established between the resonant circuit 20 and the metal medical instrument 12 means, for example, that a transmission signal is supplied from the resonant circuit 20 to the metal medical instrument 12 by an electric field and/or that a reception signal is supplied from the metal medical instrument 12 to the resonant circuit 20 by an electric field. The fact that the magnetic field coupling is established between the resonant circuit 20 and the metal medical instrument 12 means, for example, that a transmission signal is supplied from the resonant circuit 20 to the metal medical instrument 12 by a magnetic field and/or that a reception signal is supplied from the metal medical instrument 12 to the resonant circuit 20 by a magnetic field. The fact that the electromagnetic field coupling is established between the resonant circuit 20 and the metal medical instrument 12 means, for example, that a transmission signal is supplied from the resonant circuit 20 to the metal medical instrument 12 by an electromagnetic field and/or that a reception signal is supplied from the metal medical instrument 12 to the resonant circuit 20 by an electromagnetic field.

In an exemplary aspect, the metal medical instrument 12 is configured to emit the transmission signal, which has a frequency equal to the resonant frequency f0 and supplied from the resonant circuit 20, as an electromagnetic wave.

More specifically, the wireless IC chip 18 is configured to generate a transmission signal obtained by modulating a carrier wave having a frequency equal to the resonant frequency f0 with transmission data. The resonant circuit 20 resonates by the transmission signal supplied from the wireless IC chip 18. As a result, the inductor L generates a magnetic flux extending in the left-right direction. This magnetic flux makes a circle around the metal medical instrument 12 when viewed in the backward direction. Therefore, magnetic field coupling is established between the resonant circuit 20 and the metal medical instrument 12. As a result, a current flows through the metal medical instrument 12 in the front-back direction. However, a direction of the magnetic flux varies at the resonant frequency f0, a direction of the current also varies at the resonant frequency f0. In this manner, the resonant circuit 20 is configured to supply the transmission signal having the frequency equal to the resonant frequency f0 to the metal medical instrument 12. The strength of a signal having a frequency other than the resonant frequency f0, supplied from the resonant circuit 20 to the metal medical instrument 12, is lower than the strength of the transmission signal having the frequency equal to the resonant frequency f0 supplied from the resonant circuit 20 to the metal medical instrument 12. The metal medical instrument 12 is configured to emit the transmission signal supplied from the resonant circuit 20 as the electromagnetic wave. That is, the metal medical instrument 12 is configured to function as an antenna that emits the electromagnetic wave. At this time, the metal medical instrument 12 emits the electromagnetic wave from the entire metal medical instrument 12. A reader/writer 100 receives the electromagnetic wave, thereby receiving the transmission signal. In the present specification, the transmission signal having the frequency equal to the resonant frequency f0 includes a case where the frequency of the transmission signal completely coincides with the resonant frequency f0 and a case where the frequency of the transmission signal is a frequency slightly deviated from the resonant frequency f0. For purposes of this disclosure, it is noted that the slight deviation from the resonant frequency f0 means, for example, a deviation of about several tens of MHz.

The metal medical instrument 12 is further configured to receive a reception signal having a frequency equal to the resonant frequency f0 as an electromagnetic wave, and to supply the reception signal to the resonant circuit 20.

More specifically, the reader/writer 100 emits a reception signal, obtained by modulating a carrier wave having a frequency equal to the resonant frequency f0 with reception data, as an electromagnetic wave. The metal medical instrument 12 receives the reception signal, obtained by modulating the carrier wave having the frequency equal to the resonant frequency f0 with reception data, as the electromagnetic wave. That is, the metal medical instrument 12 is configured to function as an antenna that receives the electromagnetic wave. At this time, a current flows through the metal medical instrument 12 in the front-back direction.

However, a direction of the current flowing through the metal medical instrument 12 also varies at the resonant frequency f0 since the direction of the magnetic field received by the metal medical instrument 12 varies at the resonant frequency f0. As a result, the magnetic field making a circle around the metal medical instrument 12 is generated by electromagnetic induction when viewed in the backward direction. This magnetic field passes through the inductor L in the left-right direction. In addition, a direction of the magnetic field passing through the inductor L varies at the resonant frequency f0. As a result, the resonant circuit 20 resonates by the magnetic field passing through the inductor L in the left-right direction, and supplies the reception signal having the frequency equal to the resonant frequency f0 to the wireless IC tag 14. At this time, the strength of a signal having a frequency other than the resonant frequency f0, supplied from the metal medical instrument 12 to the resonant circuit 20, is lower than the strength of the reception signal having the frequency equal to the resonant frequency f0 supplied from the metal medical instrument 12 to the resonant circuit 20. The resonant circuit 20 resonates by the reception signal supplied from the metal medical instrument 12. The resonant circuit 20 supplies the reception signal having the frequency equal to the resonant frequency f0 to the wireless IC chip 18. The wireless IC chip 18 demodulates the reception signal to acquire the reception data. In the present specification, the reception signal having the frequency equal to the resonant frequency f0 includes a case where the frequency of the reception signal completely coincides with the resonant frequency f0 and a case where the frequency of the reception signal is a frequency slightly deviating from the resonant frequency f0. The slight deviation from the resonant frequency f0 means, for example, a deviation of about several tens of MHz.

It is noted that the wireless IC tag-attached metal medical instrument 10a receives, for example, the reception signal transmitted from the reader/writer 100, and reflects a part of the reception signal to transmit the transmission signal. Specifically, function (B) is performed by the metal medical instrument 12 in the wireless IC tag-attached metal medical instrument 10a. As a result, the wireless IC chip 18 demodulates the reception signal to acquire the reception data. In response, the wireless IC chip 18 generates a transmission signal obtained by modulating a carrier wave of the reception signal, received by the metal medical instrument 12, with transmission data. The resonant circuit 20 resonates by the transmission signal supplied from the wireless IC chip 18. The resonant circuit 20 supplies the transmission signal having the frequency equal to the resonant frequency f0 to the metal medical instrument 12. Thereafter, the metal medical instrument 12 performs function (A).

Meanwhile, there is a case where a wireless IC tag-attached article and a reader/writer communicate with each other via a magnetic field. In such communication via the magnetic field, a high-frequency signal belonging to a HF frequency band is used. Therefore, a coil antenna is connected to a wireless IC tag. Then, magnetic field coupling is established between the reader/writer and the coil antenna so that the reader/writer and the wireless IC tag-attached article communicate with each other. On the other hand, the wireless IC tag-attached metal medical instrument 10a communicates with the reader/writer 100 via the electromagnetic wave. That is, the wireless IC tag-attached metal medical instrument 10a communicates with the reader/writer 100 via a high-frequency signal belonging to the UHF frequency band. Therefore, the metal medical instrument 12 emits the electromagnetic wave instead of the magnetic field. The metal medical instrument 12 is not a coil antenna. Therefore, the metal medical instrument 12 does not have a coil shape. That is, the metal medical instrument 12 does not have a spiral shape or a helix shape.

In addition, the metal medical instrument 12 may have or does not necessarily have an electrical length equal to an integral multiple of a half wavelength of the resonant frequency f0. When the metal medical instrument 12 has the electrical length equal to the integral multiple of the half wavelength of resonant frequency f0, the metal medical instrument 12 functions as a dipole antenna. As a result, a standing wave is generated in the metal medical instrument 12. For example, when the metal medical instrument 12 has an electrical length equal to the half wavelength of the resonant frequency f0, the resonant frequency f0 coincides with a resonant frequency of the metal medical instrument 12.

Meanwhile, the wireless IC tag-attached metal medical instrument 10a is excellent in that the high-frequency signal can be transmitted and/or received regardless of the electrical length of the metal medical instrument 12. That is, the wireless IC tag-attached metal medical instrument 10a can be configured to transmit and/or receive the high frequency signal even when the electrical length of the metal medical instrument 12 is not equal to the integral multiple of the half wavelength of the resonant frequency f0. In order for the wireless IC tag-attached metal medical instrument 10a to exhibit such an advantage, the frequency of the transmission signal and the frequency of the reception signal are equal to the resonant frequency f0 of the resonant circuit 20 in the wireless IC tag-attached metal medical instrument 10a. Further, the resonant circuit 20 also functions as a matching circuit that achieves impedance matching between the wireless IC chip 18 and the metal medical instrument 12. Thus, the impedance of the resonant circuit 20 is equal to the impedance of the wireless IC chip 18. Further, the electric field coupling, magnetic field coupling, or electromagnetic field coupling is established between the resonant circuit 20 and the metal medical instrument 12. Thus, the resonant circuit 20 and the metal medical instrument 12 are not electrically conducted. Accordingly, the relatively weak electric field coupling, magnetic field coupling, or electromagnetic field coupling is established between the resonant circuit 20 and the metal medical instrument 12. As a result, the resonant frequency f0 of the resonant circuit 20 and the impedance of the resonant circuit 20 hardly vary even if the electrical length of the metal medical instrument 12 varies. As a result, the resonant circuit 20 resonates by the high-frequency signal having the resonant frequency f0 regardless of the electrical length of the metal medical instrument 12. Further, the impedance matching between the wireless IC chip 18 and the metal medical instrument 12 is easily achieved regardless of the electrical length of the metal medical instrument 12. Accordingly, the wireless IC tag-attached metal medical instrument 10a can transmit and/or receive the high-frequency signal having the frequency of the resonant frequency f0 regardless of the electrical length of the metal medical instrument 12. It is noted that the wireless IC tag 14 may include the matching circuit separately from the resonant circuit 20. However, no matching circuit is provided outside the resonant circuit 20 in the exemplary embodiment.

As described above, the resonance at the resonant frequency f0 hardly occurs in the metal medical instrument 12 when the electrical length of the metal medical instrument 12 is not equal to the integral multiple of the half wavelength of the resonant frequency f0. That is, a standing wave having a length equal to the half wavelength of the resonant frequency f0 is hardly generated in the metal medical instrument 12. In this case, the resonant frequency f0 is different from a frequency of the standing wave that can be generated in the metal medical instrument 12. From the above viewpoint, the metal medical instrument 12 does not necessarily have the electrical length equal to the integral multiple of the half wavelength of the resonant frequency f0.

Technical Effects

According to the wireless IC tag-attached metal medical instrument 10a, variations in communication distance of the wireless IC tag-attached metal medical instrument 10a can be suppressed. More specifically, in the wireless IC tag-attached metal medical instrument 10a, the wireless IC tag 14 is fixed to the first body portion 140 or the second body portion 142, such that at least a part of the wireless IC tag 14 is positioned more frontward than the front end P1 of the first ring portion 146 and the front end P2 of the second ring portion 148 and more backward than the support portion 144 when the first end t1 and the third end t3 are closest to each other, and the winding axis Ax of the inductor L is orthogonal to the up-down direction and intersects the front-back direction when the first end t1 and the third end t3 are closest to each other. Thus, the electric field coupling, magnetic field coupling, or electromagnetic field coupling is established between the resonant circuit 20 and the metal medical instrument 12. Hereinafter, a region located more frontward than the front end P1 of the first ring portion 146 and the front end P2 of the second ring portion 148 and more backward than the support portion 144 is referred to as a first region A. The first region A of the first body portion 140 and the second body portion 142 has a thin rod shape, and thus, often has a thin flat portion. A difficulty level of fixing the wireless IC tag 14 to the thin flat portion is slightly higher than a difficulty level of fixing the wireless IC tag 14 to a wide flat portion. However, a direction of the wireless IC tag 14 to which the wireless IC tag 14 can be fixed is limited in the thin flat portion. Thus, a difficulty level of fixing the wireless IC tag 14 to the thin flat portion in an accurate direction is lower than a difficulty level of fixing the wireless IC tag 14 to the wide flat portion in an accurate direction. As a result, the wireless IC tag 14 is fixed to the metal medical instrument 12 in the accurate direction, the variations in the communication distance of the wireless IC tag-attached metal medical instrument 10a is suppressed.

Further, in the wireless IC tag-attached metal medical instrument 10a, the wireless IC tag 14 is fixed to the first body portion 140 or the second body portion 142, such that the winding axis Ax of the inductor L of the wireless IC tag 14 is orthogonal to the up-down direction and intersects the front-back direction. As a result, the inductor L of the wireless IC tag 14 can be effectively coupled with the first body portion 140 or the second body portion 142. More specifically, when the winding axis Ax of the inductor L of the wireless IC tag 14 is orthogonal to the up-down direction and intersects the front-back direction, the winding axis Ax of the inductor L of the wireless IC tag 14 intersects the first region A of the first body portion 140 and the second body portion 142. As a result, a magnetic flux generated by the inductor L of the wireless IC tag 14 makes a circle around the first region A of the first body portion 140 and the second body portion 142. Moreover, a current is easily generated in the first region A of the first body portion 140 and the second body portion 142 by electromagnetic induction. As a result, the metal medical instrument 12 is configured to easily function as the antenna. As described above, the occurrence of the variations in the communication distance of the wireless IC tag-attached metal medical instrument 10a is suppressed.

In addition, the winding axis Ax of the inductor L is orthogonal to the up-down direction and the front-back direction when the first end t1 and the third end t3 are closest to each other according to the wireless IC tag-attached metal medical instrument 10a. Thus, the current is more easily generated in the first region A of the first body portion 140 and the second body portion 142 by electromagnetic induction. As a result, the metal medical instrument 12 is configured to easily function as the antenna. Accordingly, the occurrence of the variations in the communication distance of the wireless IC tag-attached metal medical instrument 10a is suppressed.

According to the wireless IC tag-attached metal medical instrument 10a, the wireless IC tag 14 may be fixed to the first body portion 140 or the second body portion 142 of the metal medical instrument 12 with the resin adhesive, and thus, a fixing member or the like for fixing the wireless IC tag 14 to the first body portion 140 or the second body portion 142 is unnecessary. Thus, it is easy to fix the wireless IC tag 14 to the first body portion 140 or the second body portion 142.

According to the wireless IC tag-attached metal medical instrument 10a, the wireless IC tag 14 may be fixed to the first body portion 140 or the second body portion 142 of the metal medical instrument 12 by welding, and thus, detachment of the wireless IC tag 14 from the first body portion 140 or the second body portion 142 due to an environmental change, such as a temperature change, is reduced.

(First Modification)

Figure 5:
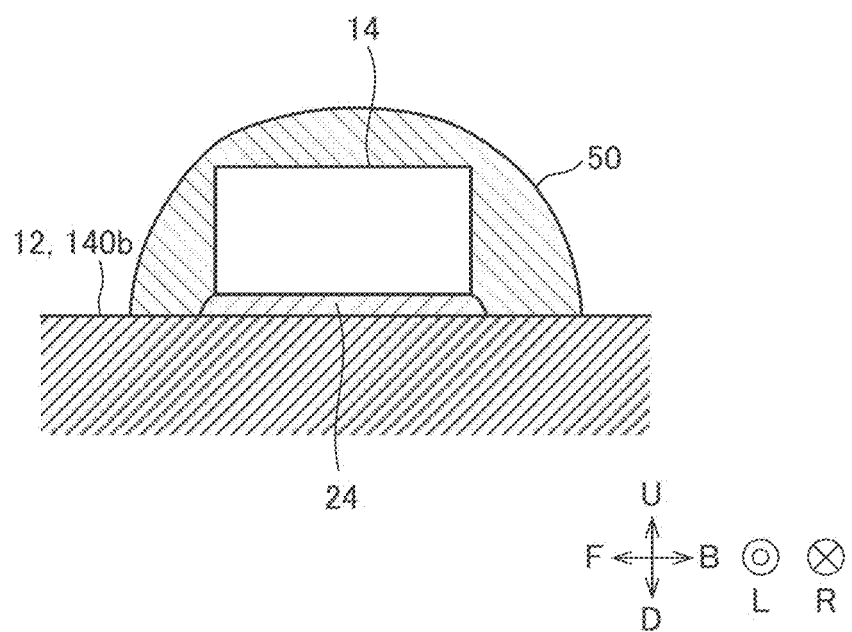
FIG. 5 is a cross-sectional view of a wireless IC tag-attached metal medical instrument 10b according to a first modification of the exemplary embodiment.

Next, a wireless IC tag-attached metal medical instrument 10b according to a first modification of the exemplary embodiment will be described with reference to the drawings. FIG. 5 is a cross-sectional view of the wireless IC tag-attached metal medical instrument 10b according to the first modification of the exemplary embodiment.

The wireless IC tag-attached metal medical instrument 10b is different from the wireless IC tag-attached metal medical instrument 10a in terms of further including a resin portion 50. The resin portion 50 covers the wireless IC tag 14 so that the wireless IC tag 14 is not exposed. Other configurations of the wireless IC tag-attached metal medical instrument 10b are the same as those of the wireless IC tag-attached metal medical instrument 10a, and thus, the description thereof will be omitted.

According to the wireless IC tag-attached metal medical instrument 10b, the occurrence of variations in communication distance of the wireless IC tag-attached metal medical instrument 10b can be suppressed for the same reason as that in the wireless IC tag-attached metal medical instrument 10a. In addition, according to the wireless IC tag-attached metal medical instrument 10b, it is easy to fix the wireless IC tag 14 to the first body portion 140 or the second body portion 142 for the same reason as that in the wireless IC tag-attached metal medical instrument 10a.

According to the wireless IC tag-attached metal medical instrument 10b, the wireless IC tag 14 is protected by the resin portion 50.

(Second Modification)

Figure 6:
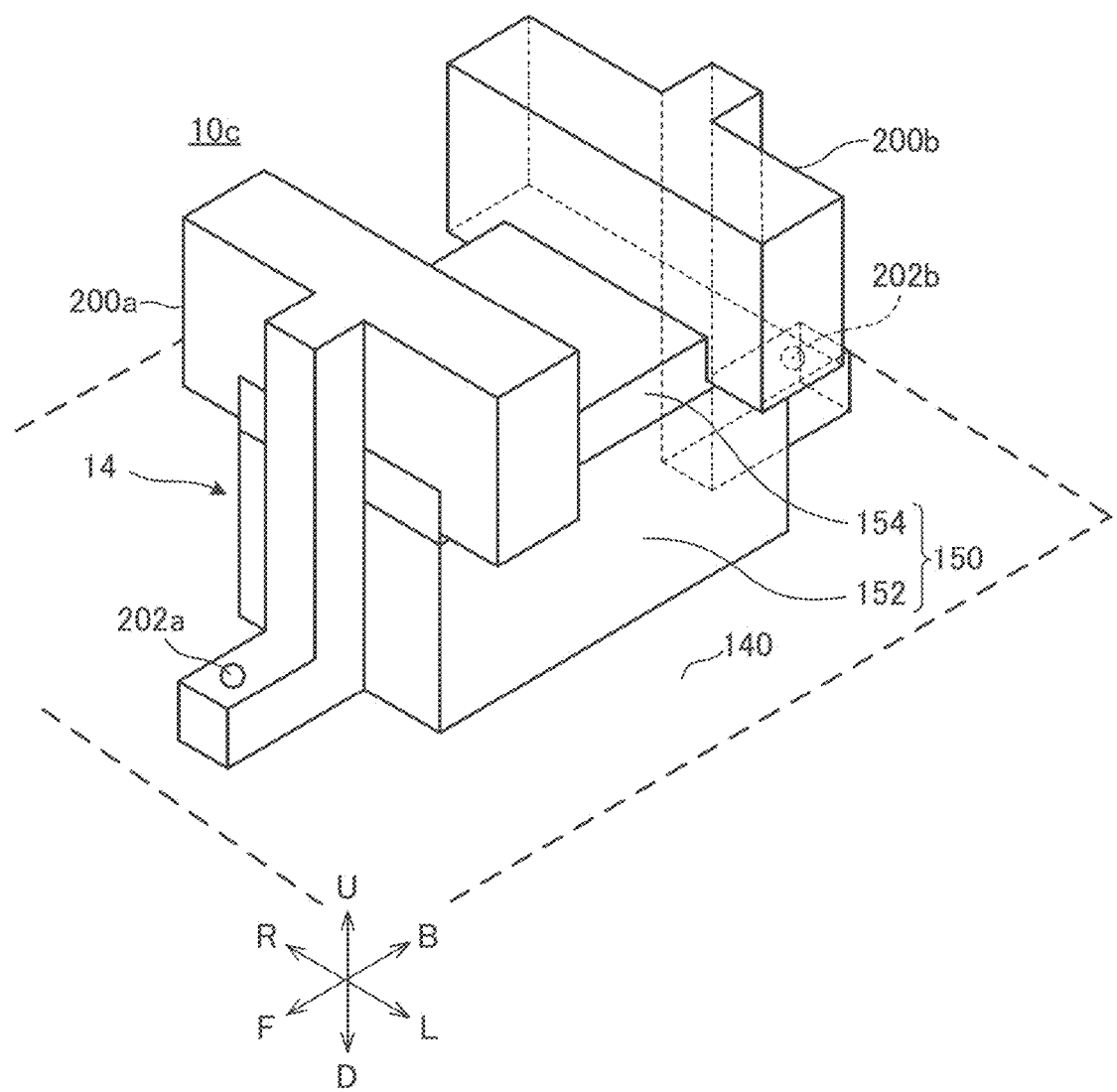
FIG. 6 is an external perspective view of the wireless IC tag 14 of a wireless IC tag-attached metal medical instrument 10c according to a second modification of the exemplary embodiment.

Next, a wireless IC tag-attached metal medical instrument 10c according to a second modification of the exemplary embodiment will be described with reference to the drawings. FIG. 6 is an external perspective view of the wireless IC tag 14 of the wireless IC tag-attached metal medical instrument 10c according to the second modification of the exemplary embodiment.

The wireless IC tag-attached metal medical instrument 10c is different from the wireless IC tag-attached metal medical instrument 10a in terms of a method for fixing the wireless IC tag 14. More specifically, the wireless IC tag 14 is fixed to the first body portion 140 or the second body portion 142 by welding in the wireless IC tag-attached metal medical instrument 10c. The wireless IC tag-attached metal medical instrument 10c includes fixing members 200a and 200b. The wireless IC tag 14 is fixed to the first body portion 140 or the second body portion 142 via the fixing members 200a and 200b welded to the first body portion 140 or the second body portion 142. In the present embodiment, the wireless IC tag 14 is fixed to the first body portion 140 via the fixing members 200a and 200b welded to the first body portion 140.

The fixing members 200a and 200b are metal members. The fixing member 200a is in contact with an upper surface and a front surface of the body 150 of the wireless IC tag 14. Then, a front end portion of the fixing member 200a is fixed to the first body portion 140 via a welded portion 202a. Therefore, the welded portion 202a where the fixing member 200a is welded to the first body portion 140 is positioned in front of the wireless IC tag 14.

The fixing member 200b has the same structure as the fixing member 200a. Specifically, the fixing member 200b is in contact with the upper surface and a back surface of the body 150 of the wireless IC tag 14. Then, a back end portion of the fixing member 200b is fixed to the first body portion 140 via a welded portion 202b. Therefore, the welded portion 202b where the fixing member 200b is welded to the first body portion 140 is positioned at the back of the wireless IC tag 14.

It is noted that the wireless IC tag 14 may be covered with a resin portion (not illustrated in FIG. 6) in an alternative aspect.

It is also noted that the wireless IC tag 14 may be fixed to the second body portion 142 via the fixing members 200a and 200b. In this case, the welded portion 202a where the fixing member 200a is welded to the second body portion 142 is positioned in front of the wireless IC tag 14. The welded portion 202b where the fixing member 200b is welded to the second body portion 142 is positioned at the back of the wireless IC tag 14.

According to the wireless IC tag-attached metal medical instrument 10c, the occurrence of variations in communication distance of the wireless IC tag-attached metal medical instrument 10c can be suppressed for the same reason as that in the wireless IC tag-attached metal medical instrument 10a. According to the wireless IC tag-attached metal medical instrument 10c, the wireless IC tag 14 is protected by the resin portion for the same reason as that in the wireless IC tag-attached metal medical instrument 10b.

According to the wireless IC tag-attached metal medical instrument 10c, detachment of the wireless IC tag 14 from the first body portion 140 or the second body portion 142 due to an environmental change, such as a temperature change, is reduced.

Additional Embodiments

The embodiment and examples for which at least one of the description and illustration has been given in the present specification are intended to facilitate the understanding of the present disclosure, and do not limit an idea of the present disclosure. The above embodiment and examples can be changed and improved without departing from a spirit thereof.

It is noted that the spirit includes equivalent elements, modifications, deletions, combinations (for example, combinations of features across the embodiment and examples), improvements, and changes that can be recognized by those skilled in the art based on the embodiment and examples disclosed herein. Such embodiment and examples should be construed to be non-exclusive. For example, in the present specification, the terms "preferably" and "preferable" are non-exclusive terms, and mean that "it is preferred but does not impose any limitation thereon" and "it is preferable but does not impose any limitation thereon".

REFERENCE SIGNS LIST 10a to 10c wireless IC tag-attached metal medical instrument
12 metal medical instrument
14 wireless IC tag
18 wireless IC chip
20 resonant circuit
24 resin adhesive
50 resin portion
100 reader/writer
140 first body portion
140a first supported portion
140b first straight portion
140c first blade portion
142 second body portion
142a second supported portion
142b second straight portion
142c second blade portion
144 support portion
146 first ring portion
148 second ring portion
150 body
152 body lower portion
154 body upper portion
200a, 200b fixing member
202a, 202b welded portion
A first region
Ax winding axis
C capacitor
L inductor
P1, P2 front end
t1 first end
t2 second end
t3 third end
t4 fourth end

The invention claimed is:

1. A wireless IC tag-attached metal medical instrument comprising:
a wireless IC tag including a resonant circuit having an inductor, and a wireless IC chip, with the resonant circuit being electrically connected to the wireless IC chip and having a predetermined resonant frequency; and
a metal medical instrument that includes:
a first body that is metal and has a first end and a second end;
a second body part that is metal and has a third end and a fourth end;
a support portion having a central axis that extends in an up-down direction and that supports the first body and the second body, such that a distance between the first end and the third end and a distance between the second end and the fourth end change as the first body rotates about the central axis relative to the second body, with the support portion also supporting the first body and the second body, such that the first body and the second body extend in a front-back direction when the first end is closest to the third end;

a first ring connected to the first end of the first body; and a second ring connected to the third end of the second body, wherein electric field coupling, magnetic field coupling, or electromagnetic field coupling is established between the resonant circuit and the metal medical instrument, such that the metal medical instrument is configured to emit a transmission signal or receive a reception signal when the wireless IC tag is fixed to the first body or the second body with at least a part of the wireless IC tag being positioned more frontward than a front end of the first ring and a front end of the second ring and more backward than the support portion when the first end is closest to the third end, and wherein a winding axis of the inductor is orthogonal to the up-down direction and intersects the front-back direction when the first end is closest to the third end.

2. The wireless IC tag-attached metal medical instrument according to claim 1, wherein the metal medical instrument is configured to emit the transmission signal having a frequency equal to the predetermined resonant frequency and that is supplied from the resonant circuit as an electromagnetic wave.

3. The wireless IC tag-attached metal medical instrument according to claim 1, wherein the metal medical instrument is configured to receive the reception signal having a frequency equal to the predetermined resonant frequency as an electromagnetic wave, and to supply the reception signal to the resonant circuit.

4. The wireless IC tag-attached metal medical instrument according to claim 1, wherein the winding axis of the inductor is orthogonal to the up-down direction and the front-back direction when the first end is closest to the third end.

5. The wireless IC tag-attached metal medical instrument according to claim 1, wherein the metal medical instrument is a medical device belonging to Class I in Japanese Medical Device Nomenclature.

6. The wireless IC tag-attached metal medical instrument according to claim 1, wherein the metal medical instrument is a steel article.

7. The wireless IC tag-attached metal medical instrument according to claim 1, further comprising a resin adhesive that fixes the wireless IC tag to the first body or the second body.

8. The wireless IC tag-attached metal medical instrument according to claim 1, wherein the wireless IC tag is fixed to the first body or the second body by a welding.

9. The wireless IC tag-attached metal medical instrument according to claim 8, wherein:

the wireless IC tag has a rectangular shape when viewed in a downward direction, a long side of the wireless IC tag extends in the front-back direction when viewed in the downward direction, the wireless IC tag is fixed to the first body or the second body via a fixing member welded to the first body or the second body, and a welded portion where the fixing member is welded to the first body or the second body is positioned in front of or at a back side of the wireless IC tag.

10. The wireless IC tag-attached metal medical instrument according to claim 1, further comprising a resin that covers the wireless IC tag so that the wireless IC tag is not externally exposed.

11. The wireless IC tag-attached metal medical instrument according to claim 1, wherein the predetermined resonant frequency is in an ultrahigh frequency (UHF) frequency band.

12. The wireless IC tag-attached metal medical instrument according to claim 1, wherein the wireless IC tag-attached metal medical instrument is configured to communicate with a reader/writer via an electromagnetic wave.

13. The wireless IC tag-attached metal medical instrument according to claim 1, wherein the wireless IC tag further includes a body having rectangular parallelepiped shape and that comprises a body lower portion formed of a plurality of insulator layers and a body upper portion disposed on the body lower portion.

14. The wireless IC tag-attached metal medical instrument according to claim 13, wherein the resonant circuit further includes a chip capacitor disposed on an upper surface of the body lower portion, and wherein the inductor is disposed in the body lower portion.

15. The wireless IC tag-attached metal medical instrument according to claim 14, wherein the inductor has a three-dimensional helix shape with the winding axis extending therethrough.

16. A wireless IC tag-attached metal medical instrument comprising:

a wireless IC tag including a wireless IC chip and a resonant circuit having an inductor; and a metal medical instrument that includes:

a first metallic body having first and second ends that oppose each other in a lengthwise direction;

a second metallic body having third and fourth ends that oppose each other in the lengthwise direction;

a support having a central axis that extends in an up-down direction orthogonal to the lengthwise direction, with the support coupling the first metallic body to the second metallic body, such that a distance between the first end and the third end and a distance between the second end and the fourth end change as the first metallic body rotates about the central axis relative to the second metallic body;

a first gripping member connected to the first end of the first metallic body; and a second gripping member connected to the third end of the second metallic body, wherein electric field coupling, magnetic field coupling, or electromagnetic field coupling is established between the resonant circuit and the metal medical instrument when the wireless IC tag is fixed to the first metallic body or the second metallic body, with at least a part of the wireless IC tag being positioned more frontward than a front end of the first gripping member and a front end of the second gripping member and more backward than the support when the first end is in a position that is closest to the third end, and wherein a winding axis of the inductor is orthogonal to the up-down direction and intersects the lengthwise direction when the first end is in the position closest to the third end.

17. The wireless IC tag-attached metal medical instrument according to claim 16, wherein the metal medical instrument is configured to emit a transmission signal or receive a reception signal when the electric field coupling, magnetic field coupling, or electromagnetic field coupling is established between the resonant circuit and the metal medical instrument.

18. The wireless IC tag-attached metal medical instrument according to claim 17, wherein the metal medical instrument is configured to emit the transmission signal having a frequency equal to a resonant frequency of an electromagnetic wave supplied from the resonant circuit.

19. The wireless IC tag-attached metal medical instrument according to claim 17, wherein the metal medical instrument is configured to receive the reception signal having a frequency equal to a resonant frequency of an electromagnetic wave from the resonant circuit, and to supply the reception signal to the resonant circuit.

20. The wireless IC tag-attached metal medical instrument according to claim 16, wherein the winding axis of the inductor is orthogonal to the up-down direction and the lengthwise direction when the first end is in the position closest to the third end.

\* \* \* \* \*